United States Patent [19]

Miike et al.

[11] Patent Number: 5,196,312
[45] Date of Patent: Mar. 23, 1993

[54] METHOD AND TEST COMPOSITION FOR DETERMINATION OF ENZYME ACTIVITY

[75] Inventors: Akira Miike, Shizuoka; Toshio Tatano, Numazu, both of Japan

[73] Assignee: Kyowa Medex Company, Ltd., Tokyo, Japan

[21] Appl. No.: 270,676

[22] Filed: Nov. 14, 1988

[30] Foreign Application Priority Data

Nov. 13, 1987 [JP] Japan .................. 62-286559

[51] Int. Cl.$^5$ .................. C12Q 1/56; C12Q 1/26
[52] U.S. Cl. .................. 435/13; 435/25
[58] Field of Search .................. 435/13, 25

[56] References Cited

U.S. PATENT DOCUMENTS

| | | | |
|---|---|---|---|
| 4,675,290 | 6/1987 | Matsumoto et al. | 435/24 |
| 4,681,841 | 7/1987 | Matsumoto et al. | 435/18 |
| 4,828,983 | 5/1989 | McClune | 435/7 |

FOREIGN PATENT DOCUMENTS

| | | |
|---|---|---|
| 0152274 | 8/1985 | European Pat. Off. . |
| 2567907 | 1/1986 | France . |
| 2162946 | 2/1986 | United Kingdom . |

*Primary Examiner*—Christine M. Nucker
*Assistant Examiner*—M. P. Woodward
*Attorney, Agent, or Firm*—Michael N. Meller

[57] ABSTRACT

Disclosed is a method for determination of an activity of γ-glutamyl transpeptidase, leucine aminopeptidase, alanine aminopeptidase, cystine aminopeptidase, X factor as a coagulation factor, thrombin, plasmin of plasminogen series, kallikrein, chymotrypsin, alkali phosphatase, N-acetyl glucosaminase and amylase, by allowing a particular substrate to act on the enzyme to thereby form an enhancer; oxidizing a chromogen by an oxidase in the presence of the enhancer and oxygen to form a pigment; and determining the pigment. Also disclosed is a test composition for carrying out the determination.

7 Claims, No Drawings

METHOD AND TEST COMPOSITION FOR DETERMINATION OF ENZYME ACTIVITY

BACKGROUND OF THE INVENTION

The present invention relates to a method and test composition for determination of an enzyme activity, and more particularly to a method for determination of an activity of an enzyme contained in a living body. The method comprises adding an appropriate substrate for an enzyme to a living body sample to thereby form a compound, which is hereinafter referred to as an enhancer, being capable of accelerating a rate of a reaction in which a chromogen is oxidized by an oxidase in the presence of oxygen; oxidizing the chromogen by the oxidase in the presence of the enhancer and oxygen to form a pigment; and quantitatively determining the pigment in a conventional manner. The present invention also pertains to a test composition suitable for carrying out such determination.

The enzyme to which the present invention is applicable includes, for example, γ-glutamyl transpeptidase (γ-GTP), leucine aminopeptidase (LAP), alanine aminopeptidase (AAP), cystine aminopeptidase (CAP), X factor as a coagulation factor, thrombin, plasmin of plasminogen series, kallikrein, chymotrypsin, alkali phosphatase, N-acetyl glucosaminase and amylase.

γ-GTP, LAP and alkali phosphatase reflect troubles of biliary and hepatic organs. AAP and N-acetyl glucosaminase are an indicator for renal disorder. CAP is an indicator for movement in uterus of a pregnant woman. X factor as a coagulation factor, thrombin and plasmin of plasminogen series are involved in coagulation of blood. Kallikrein is an indicator for primary aldosteronism and hypertension. Chymotrypsin is an indicator for chronic pancreatitis. Amylase is an indicator for pancreatic disorder.

Heretofore, determination of the activity of γ-GTP, LAP and AAP are conventionally carried out by adding a substrate for the enzyme to a sample containing the enzyme, further adding a necessary enzyme for deriving an analyzable substance from the substrate, if necessary, and measuring the rate of formation of a resulting measurable compound. For example, the activity of γ-GTP or LAP is quantitatively determined by decomposing an appropriate substrate for γ-GTP or LAP by the enzyme, thereby forming an aniline derivative, allowing the aniline derivative to react with a chromogen to thereby form a pigment, and quantitatively determining the rate of formation of the pigment. When the amount of the enzyme is small, a chromogen capable of forming a pigment having a high molecular extinction coefficient is used, but such a conventional method has a limit in determination of an activity of a trace amount of enzyme.

SUMMARY OF THE INVENTION

In accordance with the present invention, there is provided a method for determination of an enzyme activity, which comprises the steps of: (a) allowing a specific substrate for an enzyme to act on the enzyme to thereby form an enhancer; (b) oxidizing a chromogen by an oxidase in the presence of the enhancer and oxygen to thereby form a pigment; and (c) quantitatively determining the pigment in a conventional manner.

DETAILED DESCRIPTION OF THE INVENTION

In the method of the present invention, an amount of an enhancer, that is, a compound capable of increasing a rate of a reaction in which a chromogen is oxidized by the action of an oxidase in the presence of oxygen, can be quantitatively determined by quantitatively determining a pigment formed by oxidizing the chromogen by an oxidase in the presence of the enhancer and oxygen. The principle of the present invention is based on the finding that a linear relation exists between the amount of the enhancer and the rate of formation of the pigment. That is, the chromogen is oxidized by the action of an oxidase to form a pigment, and the pigment is proportionally formed to the elapse of time. At that time, if the enhancer is present, the rate of formation of the pigment is accelerated by a factor of several times to several hundred times, while keeping the proportional relation between the amount of the enhancer and the amount of the formed pigment. The present invention is based on that finding.

Even if the amount of the enzyme contained in a sample is a very small and therefore the rate of formation of the enhancer is slow, then the enhancer is gradually accumulated, the rate of formation of the pigment is gradually accelerated with an increasing amount of the accumulated enhancer, and the pigment is formed in proportion to the amount of the enhancer. By measuring the rate of formation of the pigment, the rate of formation of the enhancer can thus be quantitatively determined and consequently the activity of the enzyme contained in a sample can be quantitatively determined.

The enzyme activity is in a proportional relation to the absorbance of a colored reaction solution by formation of the pigment, and thus it is advantageous to obtain a calibration curve on the basis of the relation between the enzyme activity and the absorbance.

Quantitative determination of the thus formed pigment can be made according to any one of the known procedures. The determination is simply carried out by measuring the absorbancy of the reaction solution colored by formation of a pigment at the maximum absorption wavelength of the pigment.

In the present invention, a specific substrate is so selected that the substrate can be decomposed by the action of the enzyme whose activity to be determined to form an enhancer. In the quantitative determination of the activity of enzymes according to the present invention, such a substrate is used that the enhancer is quantitatively formed through the enzyme reaction.

Any enhancer can be quantitatively determined, so long as it is a compound capable of accelerating the rate of the reaction to oxidize a chromogen. A specific example of such an enhancer is an aniline derivative represented by the following formula (I):

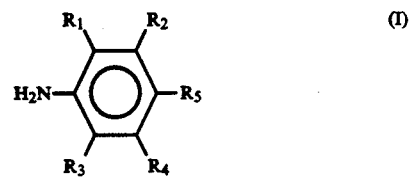

(I)

wherein $R_1$, $R_2$, $R_3$ and $R_4$ may be same or different and represent hydrogen, halogen, alkyl, sulfonyl and hydroxyl, $R_5$ represents hydroxyl, amino or substituted amino, and the substituent represents alkyl, sulfoalkyl or hydroxyalkyl.

The aniline derivative includes, for example, 3,5-dibromo-4-hydroxyaniline (DBHA), 3,5-dichloro-4-hydroxyaniline (DCHA), p-N,N-disulfopropylaminoaniline (SPA), 3,5-diiodo-4-hydroxyaniline (DIHA), 3,3-diaminostilbenzene-4,4'-disulfonic acid (DSPA), p-phenylenediamine (PPD), 4-aminoaniline-3-sulfonic acid (DAS), 2-methyl-3,5-dibromo-4-hydroxyaniline (DMBHA), 2,6-dimethyl-3,5-dichloro-4-hydroxyaniline (DMDBHA), 4-N,N-disulfopropylamino-3,5-dibromoaniline (SDBA), 4-(N-ethyl-N-hydroxyethylamino)-3,5-dibromoaniline (EHDBA), 4-N,N-diethylamino-3,4-dihydroxyaniline (DEDHA) and N,N-disulfopropylaniline (DSPA).

Any oxidase can be used in the present invention, so far as it can oxidize a chromogen in the presence of oxygen to form a pigment and includes, for example, bilirubin oxidase (BLOD, EC 1.3.3.5), monophenol monooxygenase (MPO, EC 1.14.18. 1), ascorbic acid oxidase (AOD, EC 1.10.3.3), catechol oxidase (CAO, EC 1.10.3.1), laccase (EC 1.10.3.2), o-aminophenol oxidase (APO, EC 1.10.3.4), 3-hydroxyanthranilate oxidase (HAO, EC 1.10.3.5) and phenol monooxygenase (PMO, ECl, 14, 13, 7).

Any chromogen can be used, so far as it can be oxidized to develop color. In order to obtain a higher sensitivity in the determination system, a chromogen with a higher molecular extinction coefficient is preferred. Moreover, preferred is a chromogen capable of developing color very remarkably in the presence of an enhancer, while almost never developing color through the oxidative reaction in the absence of an enhancer (which corresponds to a reagent-blank test). The chromogen includes, for example, the compounds P-1 to P-14 represented by the formulae shown in Table 1.

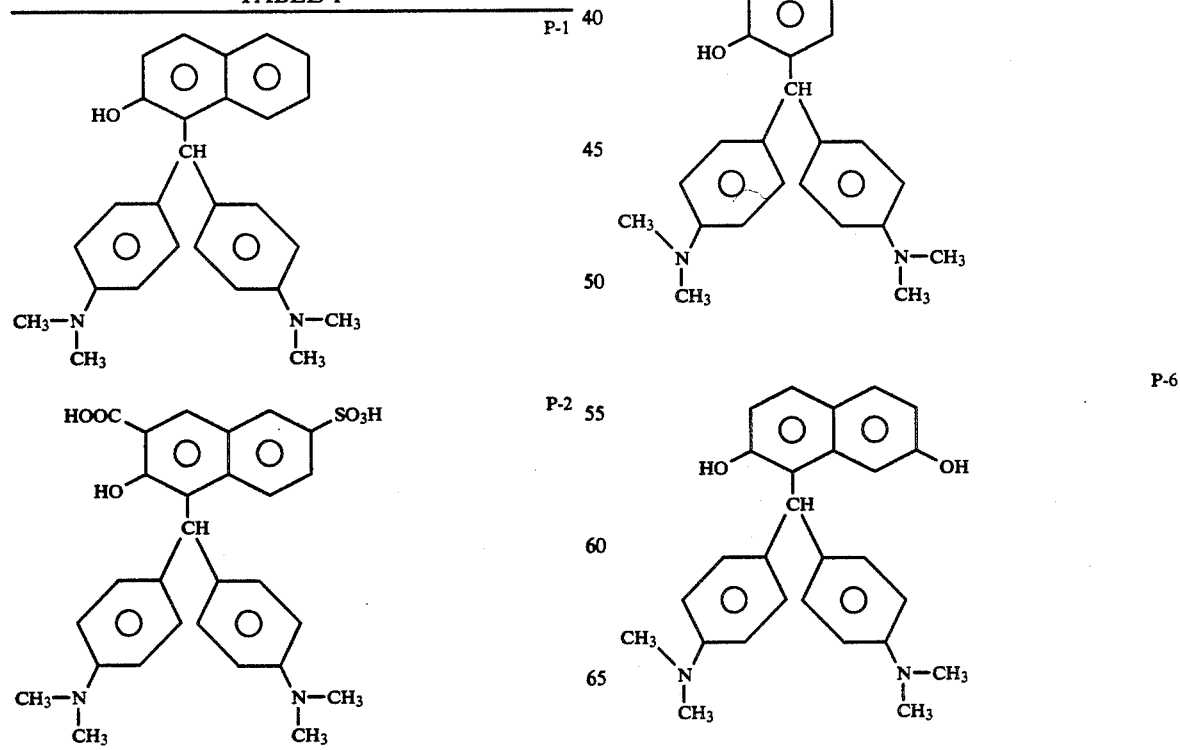

TABLE 1

TABLE 1-continued

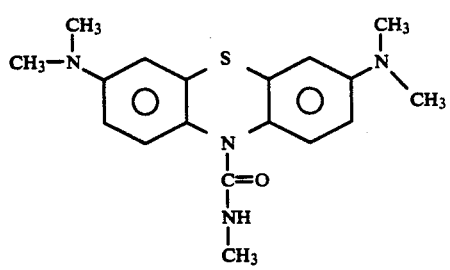 P-7

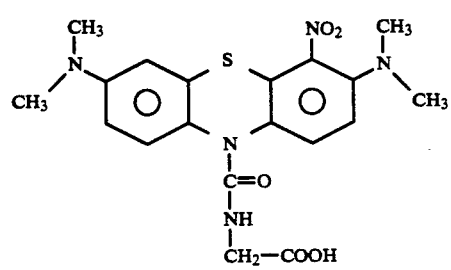 P-8

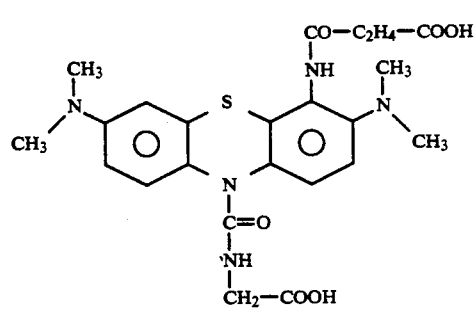 P-9

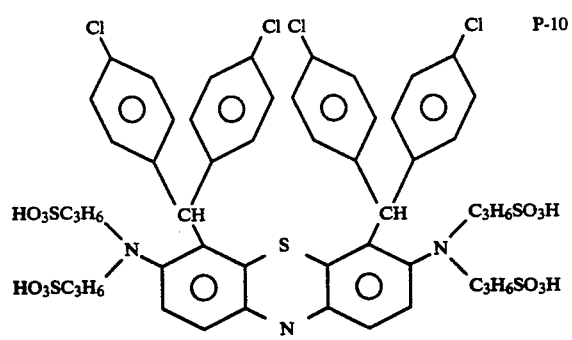 P-10

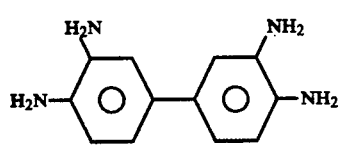 P-11

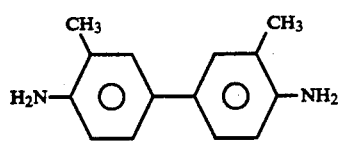 P-12

TABLE 1-continued

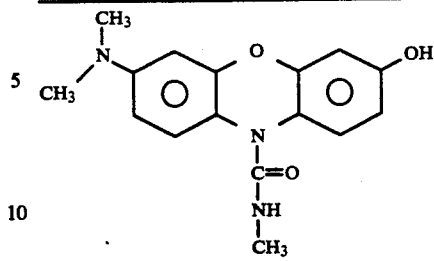 P-13

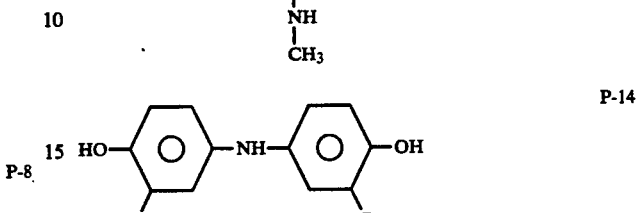 P-14

The maximum absorption of these compounds is shown in the following Table.

| Pigment No. | Maximum absorption (nm) |
|---|---|
| P-1 | 630 |
| 2 | 630 |
| 3 | 755 |
| 4 | 630 |
| 5 | 630 |
| 6 | 630 |
| 7 | 666 |
| 8 | 655 |
| 9 | 668 |
| 10 | 670 |
| 11 | 435 |
| 12 | 650 |
| 13 | 520 |
| 14 | 590 |

Chromogens P-1, P-2, P-4, P5 and P-6 are disclosed in EP-A-206316 i.e., U.S. Pat. No. 4,810,642. They are chromogens known as an intermediate for dye synthesis, and are synthesized by condensation reaction of Michler's hydrol with a naphthalene derivative or by reduction reaction of a commercially available pigment.

Chromogens P-3 and P-10 are disclosed -n EP-A-12428i.e. U.S. Pat. No. 4,916,058.

Chromogens P-7, P-8, P-9 and P-13, and the preparation thereof are disclosed in EP-B-38205 i.e., U.S. Pat. No. 4,851,353.

Chromogens P-11, P-12 and P-14 are commercially available and can be purchased from Aldrich Co.

When a substrate capable of forming an enhancer is not known as a substrate for the enzyme, a known substrate for the enzyme can be combined with an enhancer and the thus prepared substrate may be used. For example, since such an enhancer as DBHA, DCHA, etc. has a hydroxyl group, those skilled in the art can readily prepare a suitable substrate obtained by combining a known substrate with an enhancer through an appropriate amino acid or peptide.

Combinations of the enzyme with the substrate in the present invention are given below:

| Enzyme | Substrate |
|---|---|
| $\gamma$-GTP | $\gamma$-glutamyl—DBHA |
| LAP | L-leucyl—DBHA |
| AAP | L-alanyl—DBHA |
| Cystine aminopeptidase | S—Bz—Cys—DBHA |
| X factor as a coagulation | Bz—Ileu—Glu—Gly—Arg—DBHA |

-continued

| Enzyme | Substrate |
|---|---|
| factor | |
| Thrombin | D—Phe—Pip—Arg—DBHA |
| Plasmin of plasminogen series | D—Val—Leu—Lys—DBHA |
| Kallikrein | Z—Pro—Phe—Arg—DBHA |
| Chymotrypsin | Bz—Tyr—DBHA |
| Alkai phosphatase | 2,6-dibromo-4-aminophenyl phosphate |
| | 2,6-dichloro-4-aminophenyl phosphate |
| N-acetyl glucosaminase | p-aminophenyl-N-acetyl-glucosamine |
| Amylase | 2,6-diiodo-4-aminophenyl-G7 (or G5) |

In the quantitative determination of an enzyme activity, a substrate capable of forming an enhancer, a chromogen, an oxidase, a buffer reagent, a surfactant, etc. are added to a sample to carry out an enzyme reaction. In the enzyme reaction, the respective reagents are used at the following concentrations:

| Buffer reagent | 10 mM–1M |
|---|---|
| Oxidase | 0.001–1,000 U/ml |
| Chromogen | 0.01–10 mg/l |
| Substrate | 0.1–100 mg/ml |
| Surfactant | 1–10 mg/ml |

The reaction is usually carried out at a temperature of 20°–40° C. and at a pH of 5–9.

The buffer reagent for use in the present invention includes, for example, Good's buffer, phosphate, borate, acetate and tris-hydrochloride. Another aspect of the present invention is to provide a test composition for determination of an enzyme activity, which comprises a substrate capable of forming an enhancer, an oxidase and a chromogen. The composition can further contain a buffer reagent, a surfactant, etc. The aforementioned concentrations are applied to the respective components of the composition.

Sheets, films, sticks, etc. prepared by impregnating an appropriate reagent solution-adsorbable material such as a filter paper, polymer, etc. with a reagent solution necessary for the determination and drying the material, are convenient and useful for the diagnostic purpose. The adsorbable material is impregnated with the components necessary for the determination at the aforementioned concentrations and dried. A sample is dropped onto the thus prepared adsorbable material to effect the reaction, and the intensity of color development is compared with that of a reagent blank.

Certain specific embodiment of the invention are illustrated by the following representative examples.

EXAMPLE 1

| DIPSO (Good's buffer solution, made by Dojin Kagaku Kenkyusho) (pH 7.5) | 0.1M |
|---|---|
| Dispanol M-32A (made by Nihon Yushi K.K.) | 5 mg/ml |
| Compound P-1 | 0.2 mg/ml |
| BLOD | 0.02 U/ml |
| Gly—Gly | 3 mg/ml |
| MgCl$_2$ | 1 mg/ml |
| $\gamma$-glutamyl—DBHA (G-DBHA) | 2 mg/ml |

To 3.0 ml of the foregoing reagent solution was added 0.02 ml of aqueous $\gamma$-GTP solution at a concentration of 2.5, 5, 7.5 or 10 mU/ml. The mixture was allowed to stand at 37° C. for 30 minutes and changes in the absorbancy of the reaction solution at 630 nm were measured.

The reactions can be given as follows:

The amount of DBHA in the reaction solution is gradually increased, and the rate of formation of the pigment is increased with increasing amount of DBHA. By determining the amount of the thus formed pigment, the activity of $\gamma$-GTP in the reaction solution can be determined.

As a control test, the same procedure was repeated with a reagent of the same composition as described above, except that 1.5 mg/ml of N-ethyl-N-(3-methylphenyl)-N'-succinyl ethylenediamine (EMSE) was used as a chromogen in place of P-1 and that 0.4 U/ml of BLOD was used. The absorbancy of the reaction solution at 710 nm was measured.

The reactions proceed as follows:

In the foregoing reactions in which the rate of reaction is not accelerated, the formation of pigment is much retarded.

It is obvious from the test results given in the following Table that the concentration of $\gamma$-GTP and the absorbancy are in a proportional relation.

| $\gamma$-GTP (mU/ml) | 2.5 | 5 | 7.5 | 10 |
|---|---|---|---|---|
| The Invention | 0.32 | 0.67 | 1.02 | 1.35 |
| Conventional method | 0.03 | 0.06 | 0.09 | 0.12 |

EXAMPLE 2

| Reagent solution A | |
|---|---|
| DIPSO Buffer solution (pH 7.5) | 0.1M |
| Dispanol M-32A | 5 mg/ml |
| Compound P-2 | 0.2 mg/ml |
| AOD | 50 U/ml |
| MgCl$_2$ | 1 mg/ml |
| L-leucyl DSPA | 2 mg/ml |

To 3.0 ml of reagent solution A was added 0.02 ml of aqueous solution containing 20 mU/ml LAP, and then the mixture was allowed to stand for 30 minutes. The absorbancy of the reaction solution was measured at 630 nm. Likewise, as a control test, the same procedure was repeated except that EMSE was used in place of P-2, and the absorbancy of the reaction solution was measured at 745 nm.

The degree of color development of the present invention was compared to that of the control test, and that the sensitivity of the present invention was 5.2 times as high as that of the control test.

EXAMPLE 3

Reagent solution A

| Phosphate buffer solution (pH 7.2) | 0.1M |
| --- | --- |
| Triton X-100 | 5 mg/ml |
| Compound P-1 | 1 mg/ml |
| AOD | 200 mg/ml |
| γ-glutamyl-DBHA | 10 mg/ml |
| Gly—Gly | 20 mg/ml |

A Wattman No.41 filter paper with a thickness of 0.21 mm was dipped in reagent solution A and then dried in a vacuum drier to prepare test paper A.

Reagent solution B

Reagent solution B has the same component as reagent solution A except that 4 mg/ml of EMSE was used in place of Compound P-1 and that 500 U/ml of AOD was used. With the reagent solution B, test paper B was prepared in the same manner as above.

Aqueous solutions containing 0, 0.1, 0.2, 0.5, 1.0, 2.0, 5.0, 10, 20 or 50 mU/ml of γ-GTP were prepared, and 100 μl of each of the solutions was dropped onto test papers A and B to investigate up to what concentration of γ-GTP could be detected. When the reaction period was 20 minutes, test paper B could detect up to 5.0 mU/ml, whereas test paper A could detect up to 0.1 mU/ml. When the reaction period was 3 minutes, test paper B could detect up to 50 mU/m( whereas test paper A could detect up to 1 mU/ml. When urine of a normal man and urine of a patient with renal diseases were dropped onto test papers A and B, it was found that the differentiation of urine of the normal man from that of the patient was carried out over 20 minutes with test paper B, whereas over 5 minutes with test paper A.

Example 4

The same test papers A and B were prepared in the same manner as in Example 3, except that each of oxidases shown in the following Table was used in place of AOD of Example 3. Urine of a patient with renal diseases was dropped onto test papers A and B. The dropped papers were subjected to the analysis by chromatoscanner to compare the degree of color development of test paper A to that of test paper B. The ratios of the degree of color development are shown below.

| Oxidase | Concentration U/ml | Sensitivity (ratio) |
| --- | --- | --- |
| MPO | 0.2 | 16.5 |
| CAO | 1.2 | 78.1 |
| Laccase | 0.05 | 4.3 |
| APO | 0.02 | 6.9 |
| HAO | 2.5 | 9.2 |
| PMO | 0.08 | 11.6 |

EXAMPLE 5

The same procedure was repeated in the same manner as in Example 1, except that enzymes and substrates given in the following Table were used to compare the present invention A with the conventional method B.

| Enzyme to be determined | Substrate | Sensitivity ratio A/B |
| --- | --- | --- |
| CAP | S—Bz—Cys—DBHA | 10.2 |
| X factor | Bz—Ile—Glu—Gly—Arg—DBHA | 14.5 |
| Thrombin | D-Phe—Pip—Arg—DBHA | 9.8 |
| Plasmin | D-Val—Leu—Lys—DBHA | 13.5 |
| Kallikrein | Z—Pro—Phe—Arg—DBHA | 12.6 |

EXAMPLE 6

The Activity of the enzymes given in the following Table was determined in the same manner as in Example 2, except that the substrates given in the following Table were used in place of DSPA, and the ratios of sensitivity were obtained in the same way.

| Enzyme | Substrate | Sensitivity ratio A/B |
| --- | --- | --- |
| Alkali phosphatase | 2,6-dichloro-4-aminophenylphosphate | 10.6 |
| N-Acetylglucosaminase | p-aminophenyl-N-acetyl-glucosamine | 4.2 |
| Amylase | 2,6-diiodo-4-aminophenyl-G7 (or G5) | 2.8 |

EXAMPLE 7

The same procedure was repeated in the same manner as in Example 2, except that DIHA, DSDA, PPD, DAS, DMBHA, DMDBHA, SDBA, EHDBA and DEDHA were used separately in place of DSPA of Example 2, and the sensitivity ratios, A/B, were found to be 46.1, 3.4, 6.8, 4.4 16.6, 20.8, 5.0, 11.4 and 8.9, respectively.

What is claimed is:

1. A method for determination of an enzyme activity, which comprises the steps of:
   (a) allowing a substrate for the enzyme whose activity is to be determined and which is capable of releasing an aniline derivative, to act on the enzyme to thereby form the analine derivative,
   (b) oxidizing a chromogen which is capable of being oxidized without condensing with the aniline derivative by an oxidase selected from the group consisting of bilirubin oxidase, monophenol monooxygenase, ascorbic acid oxidase, catechol oxidase, laccase, o-aminophenol oxidase, 3-hydroxyanthranilate oxidase and phenol monooxygenase, in the presence of oxygen and in the absence of a coupler to be oxidatively condensed with the aniline derivative, to thereby form a pigment; and
   (c) quantitatively determining the pigment by colorimetry;
the aniline derivative being represented by the formula (I):

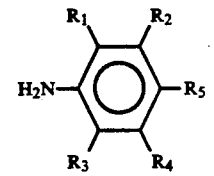

(I)

wherein $R_1$, $R_2$, $R_3$ and $R_4$ may be same or different and are selected from the group consisting of hydrogen, halogen, alkyl, sulfonyl and hydroxyl, $R_5$ is selected from the group consisting of hydroxyl, amino and substituted amino, wherein said substituent is selected from the group consisting of alkyl, sulfoalkyl and hydroxyalkyl.

2. The method according to claim 1, wherein the enzyme is selected from the group consisting of γ-glutamyl transpeptidase, leucine aminopeptidase, alanine aminopeptidase, cystine aminopeptidase, X factor as a coagulation factor, thromobin, plasmin of plasminogen series, kallikrein, chymotrypsin, alkali phosphatase, N-acetyl glucosaminase and amylase.

3. A test composition for determination of an enzyme activity, which comprises a substrate being capable of forming the aniline derivative defined in claim 1, an oxidase and a chromogen.

4. The test composition according to claim 3, wherein the composition further contains a buffer reagent and a surfactant.

5. A reagent solution-adsorbable material for diagnostic purpose, which is prepared by impregnating an adsorbable material with the test composition defined in claim 3.

6. A reagent solution-adsorbable material for diagnostic purpose, which is prepared by impregnating an adsorbable material with the test composition defined in claim 4.

7. The method according to claim 1, wherein the chromogen is selected from the group consisting of compounds P-1 to P-14 of the formulas

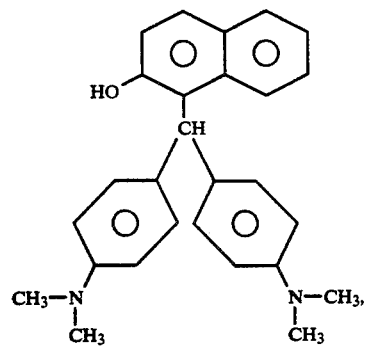

P-1

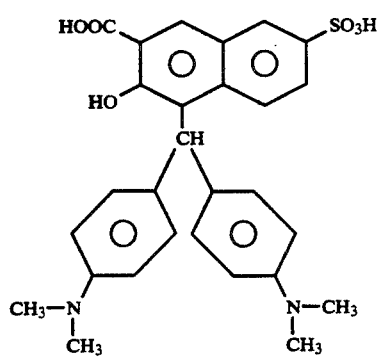

P-2

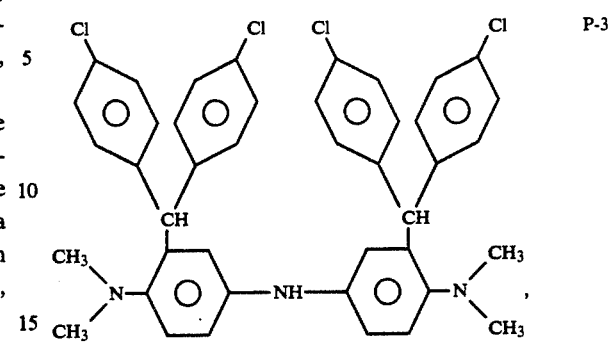

P-3

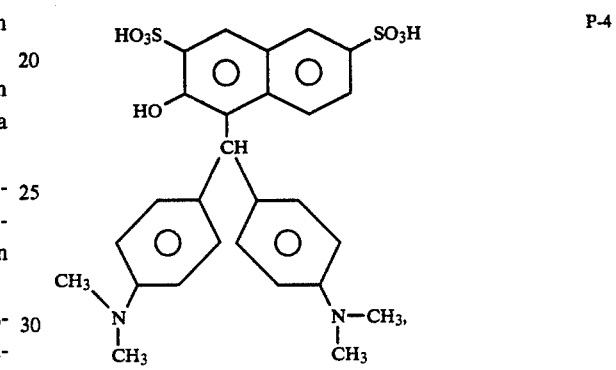

P-4

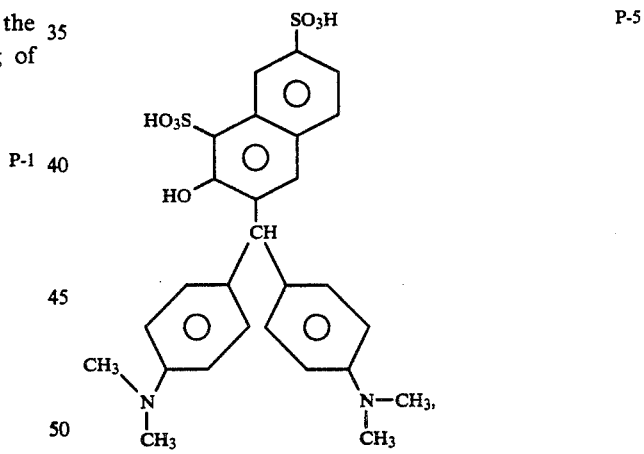

P-5

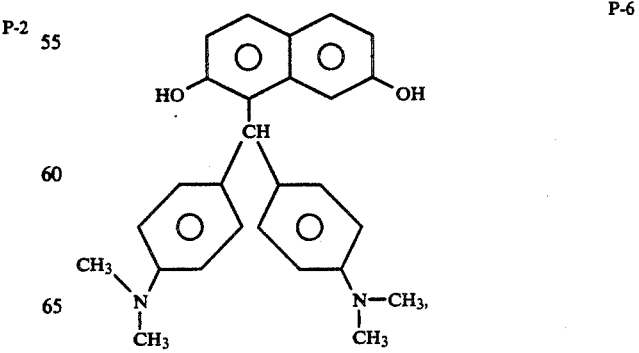

P-6

P-7
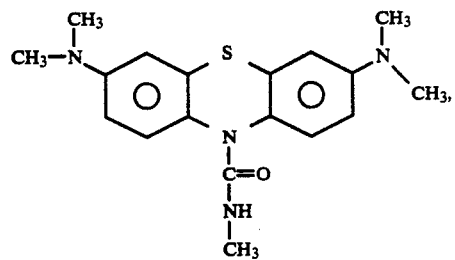
P-8
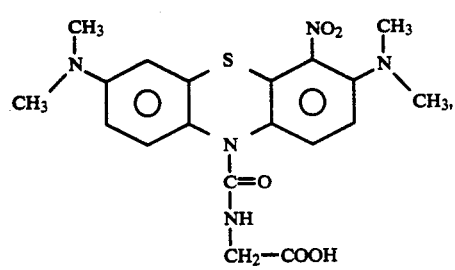
P-9
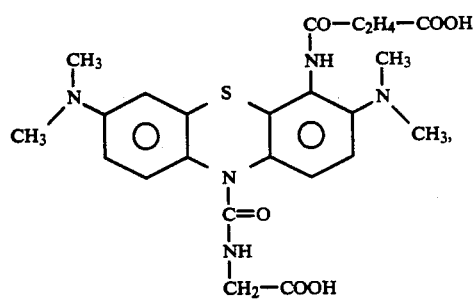
P-10
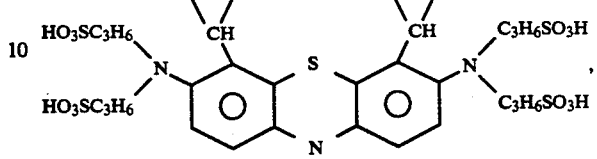
P-11
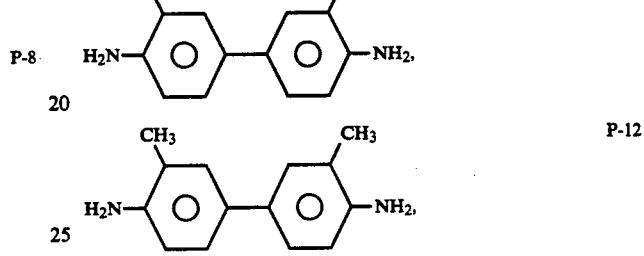
P-12
P-13
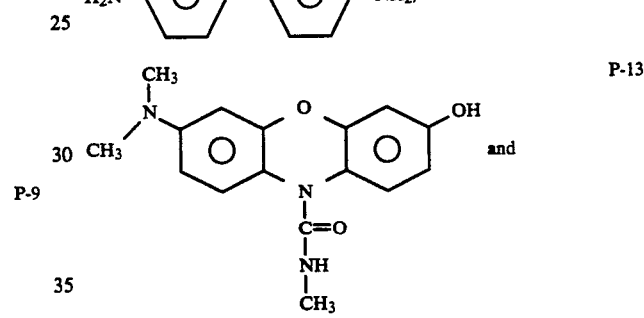
and
P-14
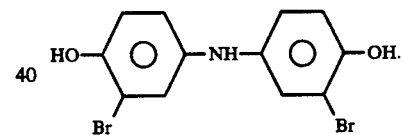
* * * * *